United States Patent [19]
Ahmed

[11] Patent Number: 5,411,473
[45] Date of Patent: May 2, 1995

[54] MEDICAL VALVE

[76] Inventor: A. Mateen Ahmed, 928 E. Juanita Ave., La Verne, Calif. 91750

[21] Appl. No.: 786,734

[22] Filed: Oct. 1, 1991

Related U.S. Application Data

[60] Division of Ser. No. 478,655, Feb. 12, 1990, Pat. No. 5,071,408, which is a continuation of Ser. No. 255,070, Oct. 7, 1988, abandoned.

[51] Int. Cl.⁶ ............................................. A61M 5/00
[52] U.S. Cl. .......................................... 604/8; 604/9; 604/294
[58] Field of Search ................ 606/108, 9; 604/11, 604/51, 8–10, 294, 164, 264; 128/768, 772; 137/844, 846

[56] References Cited

U.S. PATENT DOCUMENTS

| | | | |
|---|---|---|---|
| 3,530,860 | 9/1970 | Marjoros | 606/108 X |
| 3,598,118 | 8/1971 | Warren | 606/108 X |
| 4,211,234 | 7/1980 | Fisher | 606/108 X |
| 4,554,918 | 11/1985 | White | 604/10 |
| 4,729,761 | 3/1988 | White | 604/8 |
| 4,750,901 | 6/1988 | Molteno | 604/8 |
| 4,798,193 | 1/1989 | Giesy et al. | 606/108 |
| 4,826,478 | 5/1989 | Schock et al. | 604/8 |
| 4,968,296 | 11/1990 | Ritch et al. | 604/8 |
| 5,092,837 | 3/1992 | Ritch et al. | 604/8 |

Primary Examiner—Robert A. Hafer
Assistant Examiner—Sam Rimell
Attorney, Agent, or Firm—John J. Connors; Connors & Associates

[57] ABSTRACT

Disclosed is a medical valve comprising a pair of plates holding in tension a membrane folded over to form a chamber with an elongated, slit-like opening along adjoining edges. The plates include interlocking members which interlock the plates together. An inlet tube in communication with the chamber extends outwardly from the plates. The preferred configuration of the chamber is trapezoidal. Also disclosed is a surgical instrument that is a needle-like member having an elongated slot in the wall of this member. A method of using this instrument to implant a tubular element in the body of a patient is also disclosed.

9 Claims, 10 Drawing Sheets

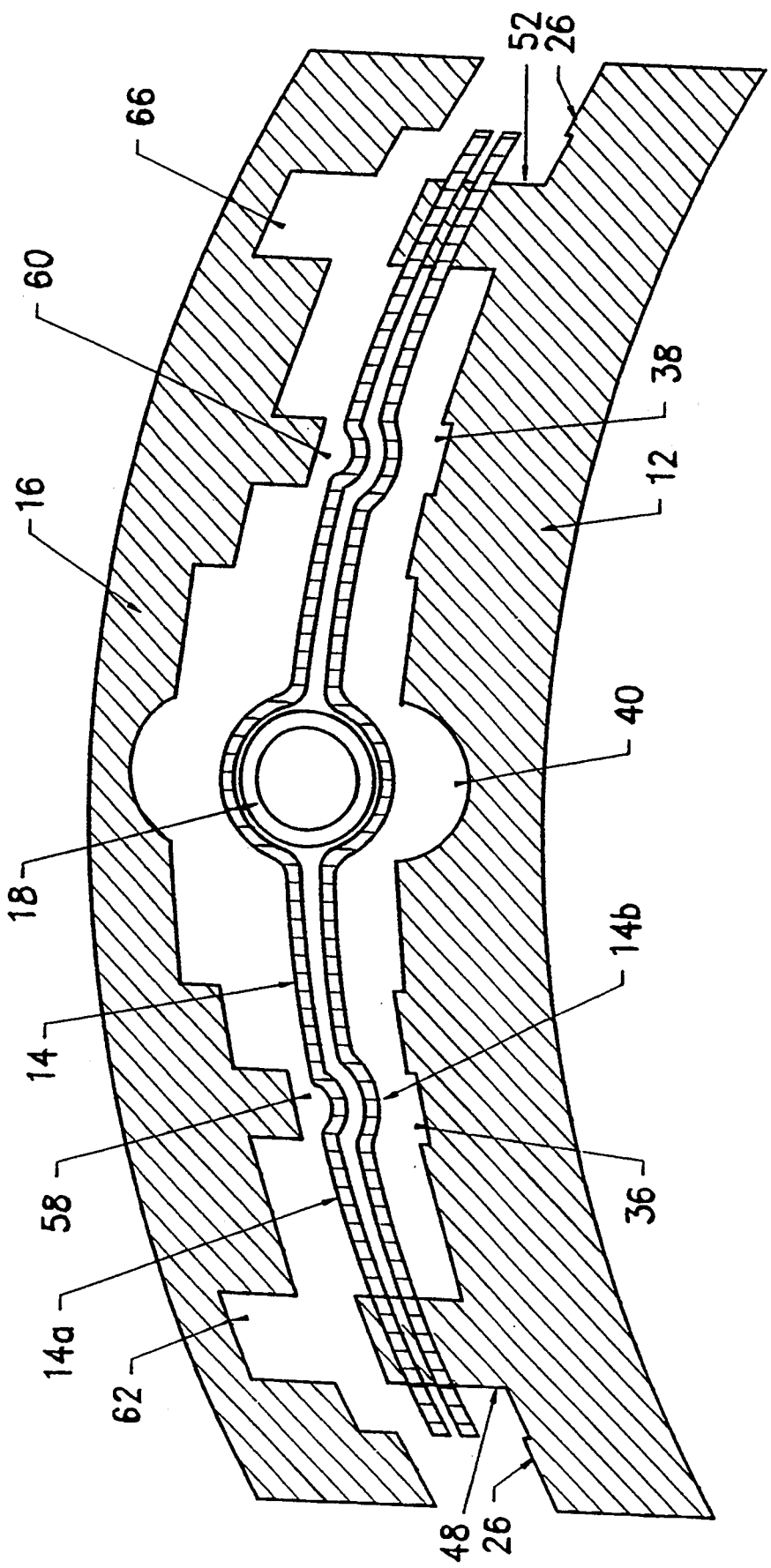

MEDICAL VALVE

This is a division of application Ser. No. 07/478,655, filed Feb.12, 1990, now U.S. Pat. No. 5,071,408, which is a continuation of application Ser. No. 07/255,070, filed Oct. 7, 1988, now abandoned.

RELATED PATENT APPLICATION

This application is a continuation-in-part application of U.S. patent application Ser. No. 07/255,070, entitled Self-Regulating Pressure Control Glaucoma Valve, filed Oct. 7, 1988, which is incorporated herein by reference and made a part of this application.

BACKGROUND OF THE INVENTION

1. Field of Invention

This invention relates to medical valves which are implanted in the human body, particular to such a valve which is easy to manufacture, performs reliably, is easy to surgically implant in the human body, and will remain functional for the life of the patient in which it is implanted.

2. Background Discussion

Medical valves are used for many different types of applications. One such application is to treat glaucoma by allowing aqueous humor to flow from the intraoccular chamber of the eye to relieve excess pressure. Thomas C. White in U.S. Pat. No. 4,554,918 has suggested one type of glaucoma valve where the aqueous humor flows from the intraoccular chamber through a tube into an external reservoir. The end of the tube in communication with the reservoir has a small opening in its end. The small opening provides a great deal of resistance to flow of the aqueous humor which is highly viscous. The white valve provides for flow in only one direction, namely, from the intraoccular chamber of the eye to the external reservoir. Upon being filled the reservoir is pressed by the patient to force the aqueous humor contained in the reservoir through another tube into the body of the patient where it is absorbed.

Another device used to treat glaucoma is discussed by Anthoney C. B. Molteno in U.S. Pat. No. 4,457,757. This device includes a plate having a tube that extends into the intraoccular chamber. The aqueous humor from the intraoccular chamber flows onto the surface of the plate and is absorbed by the body. The Molteno plate does not have any pressure controlling mechanism, and it is only a device for releasing intraoccular pressure.

Both of these devices have been used to treat glaucoma, but the white valve suffers from the disadvantage that the patient must manually press the reservoir in order to force the aqueous humor collected in the reservoir to escape and be absorbed by the body. Moreover, although the White valve is designed to open when the intraoccular pressure becomes excessive, the valve's structure is not reliable, because it depends upon a tiny opening in the end of the tube which is very small in diameter and can easily be clogged by particulates. Nor is the White valve very sensitive, because it does not respond to slight changes in pressure to open and close. The Molteno plate overcomes the objections of the manually actuated reservoir, however, it does not employ a valve and could lead to hypotony, that is, the loss of aqueous humor within the intraoccular chamber of the eye.

SUMMARY OF THE INVENTION

The present invention is a medical valve which may be implanted in the human body, and particularly a one way valve which can be used to treat glaucoma.

There are several features of this invention, no single one of which is solely responsible for its desirable attributes. Without limiting the scope of this invention as expressed by the claims, its more prominent features will now be discussed briefly. After considering this discussion, and particularly after reading the section of the application entitled "DETAILED DESCRIPTION OF THE PREFERRED EMBODIMENT," one will understand how the features of this invention provide its advantages.

The first feature of this invention is use of membrane means under tension to form a chamber having an elongated, slit-like opening therein. The membrane means responds to slight changes in pressure to expand or contract to open or close the opening. When opened, it provides a wide open mouth with parted lips that allows for free flow of fluid though it without any substantial resistance to fluid flow. This feature also substantially reduces the likelihood that the opening will be clogged by particulates. Typically the width of the slit-like opening ranges between 2.500 and 3.500 millimeters, preferably between 2.725 and 2.750 millimeters.

The second feature is that the chamber has a trapezoidal configuration to provide a narrow side and a wide side. The slit-like opening is essentially coextensive with the narrow side and an inlet tube is connected to the wide side. Fluid flows into the chamber through the inlet tube. Depending on the fluid pressure within the chamber, the slit-like opening will be either opened or closed. The pressure in the chamber must, however, exceed the tension in the membrane means in order to expand the membrane means to open the slit-like opening.

The third feature is the trapezoidal configuration of the chamber renders the valve highly responsive to slight changes in pressure. The fluid as it enters the chamber at the wide side first flows into a space which has a relatively large cross-sectional area compared to the cross-sectional area of the chamber adjacent to the slit-like opening in the narrow side. This is important because it makes the valve sensitive to slight changes in pressure and allows it to open very briefly to reduce the pressure in the chamber. When the fluid pressure in the chamber just equals the pressure created by the tension in tile membrane means, the slit-like opening is closed. As soon as this pressure increases due to additional fluid flowing into the chamber along its wide side, the membrane means expands and the fluid flows from the slit-like opening. The velocity of the fluid flowing from the opening is substantially higher than the velocity of the fluid entering the chamber at its wide side to decrease quickly the pressure in the chamber and close the valve. The relative high velocity with which the fluid exits the opening aids in flushing the chamber and reduces the possibility of back flow. Since the rate at which aqueous humor is formed in the intraoccular chamber of the eye is very slow, approximately one drop every three hours, slight increases in volume of aqueous humor result in the valve of this invention opening momentarily and then closing. These unique features of the valve of this invention allow pressure in the chamber to be maintained at 10 millimeters (mm) of mercury (Hg), with an increase in pressure of 0.5 mm of Hg opening the valve.

As soon as the intraoccular pressure stabilizes at 10.0 mm of Hg, the valve is totally shut off to prevent the further flow of aqueous humor from draining from the intraoccular chamber. Thus, the cornea never loses its dome-like shape and hypotony is avoided.

The forth feature is the use of two plates which hold between them in tension overlying membrane members which form between them the chamber. The slit-like opening is along adjoining, overlapping edges of the membranes. Preferably, the membranes are simply two halves of a thin sheet of silastic material which is folded over upon itself.

The fifth feature is that the ,two plates each include interlocking members that, upon the plates being pressed together, engage to place the membranes disposed between the plates in tension. By adjusting the size and positions of the interlocking members, the tension may be varied to provide different valve designs which open in response to different pressures. Moreover, once the tension is established for a specific valve design, this valve is easily reproducible, allowing this specific valve design to be mass produced without any significant variation in its pressure response from one valve to another. The interlocking members for any specific valve design apply essentially equal tension across the entire width of the membrane. This is desirable to insure repeatable performance.

The sixth feature is that each of the plates includes therein identical trapezoidal shaped depressions. The plates are aligned with each other when joined together so that the two trapezoidal depressions are in registration. The trapezoidal configured chamber is formed when fluid flows between the membranes to expand them outwardly, pushing the membranes outwardly against the walls of the depressions.

The seventh feature is that the valve of this invention employs a distribution plate having an enlarged surface area. Aqueous humor is caustic and the body can only gradually absorb it. This absorption process is promoted if this aqueous humor is distributed over a relative large surface. The enlarged area of the distribution plate serves this purpose. Typically the surface area of the distribution plate ranges between 0.050 and 0.250 square inches, preferably between 0.119 and 0.200 square inches.

The eighth feature is that the valve is adapted to be attached to the eye to provide a hinge-like, cantilever action. A pair of suturing holes are provided on the main body of the valve, one hole on each side of the inlet tube. When the valve is placed on the eye, two stitches are made, one through each hole to secure the valve to the sclara of the eye. This creates a large distribution area under the valve to be used for absorption of the aqueous humor.

The ninth feature is that a novel surgical instrument and method have been invented to implant a tube in the body of the patient. The surgical instrument is a needle-like member having a length and diameter corresponding to conventional needles. The unique feature of this instrument is that it includes an elongated channel along its longitudinal axis with an elongated slot in the wall of the needle that provides access to the channel. The width of the slot and the diameter of the channel are essentially equal to the diameter of the tube being implanted in the body of the patient. The slot, with its width dimension equaling the diameter of the tube, permits the tube to be placed lengthwise in the channel so that the wall of the tube and the wall of the channel engage frictionally. Thus, fluid does not readily flow between these walls but rather flows through the tube. The frictional fit, however, is not so tight that the tube is prevented from sliding through the slot upon removal of the instrument from the body of the patient. Thus, when the tip of the instrument is inserted into the body of the patient the body tissue grasps the tube. Then when the instrument is removed, the tube remains in the body of the patient, passing through the slot as the instrument is removed.

DESCRIPTION OF THE DRAWING

The preferred embodiment of this invention illustrating all of its features will now be discussed in detail. This embodiment depicts the novel and unobvious features of the medical valve of this invention. The drawing accompanying this application, which is for illustrative purposes only, includes the following figures (Fig.) with like numerals indicating like parts:

FIG. 3A is a cross-sectional view showing the two plates positioned to be press together to hold the folded membrane therebetween.

DETAILED DESCRIPTION OF THE PREFERRED EMBODIMENT

Figure 1:
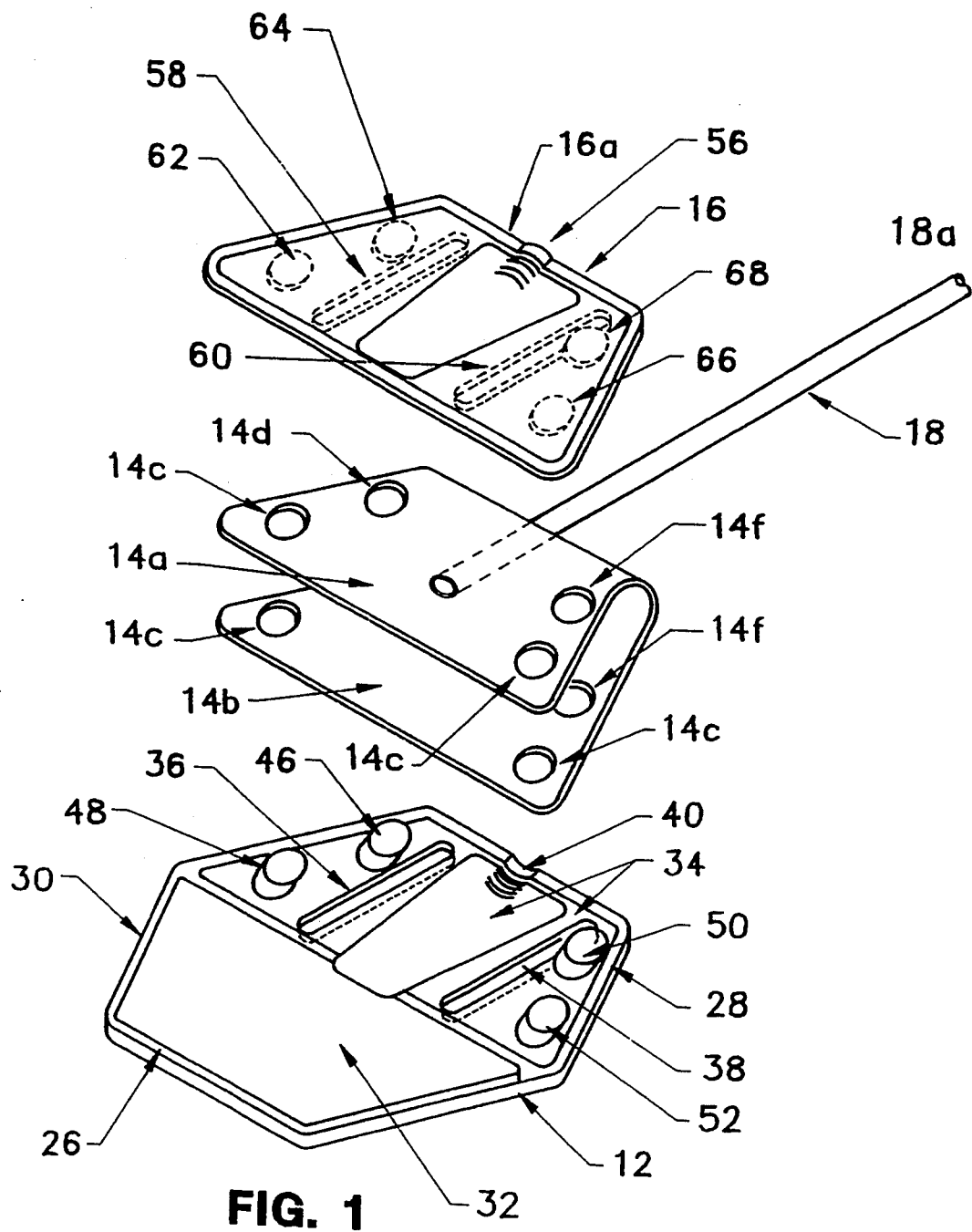
FIG. 1 is an exploded perspective view of the medical valve of this invention.
Figure 3B:
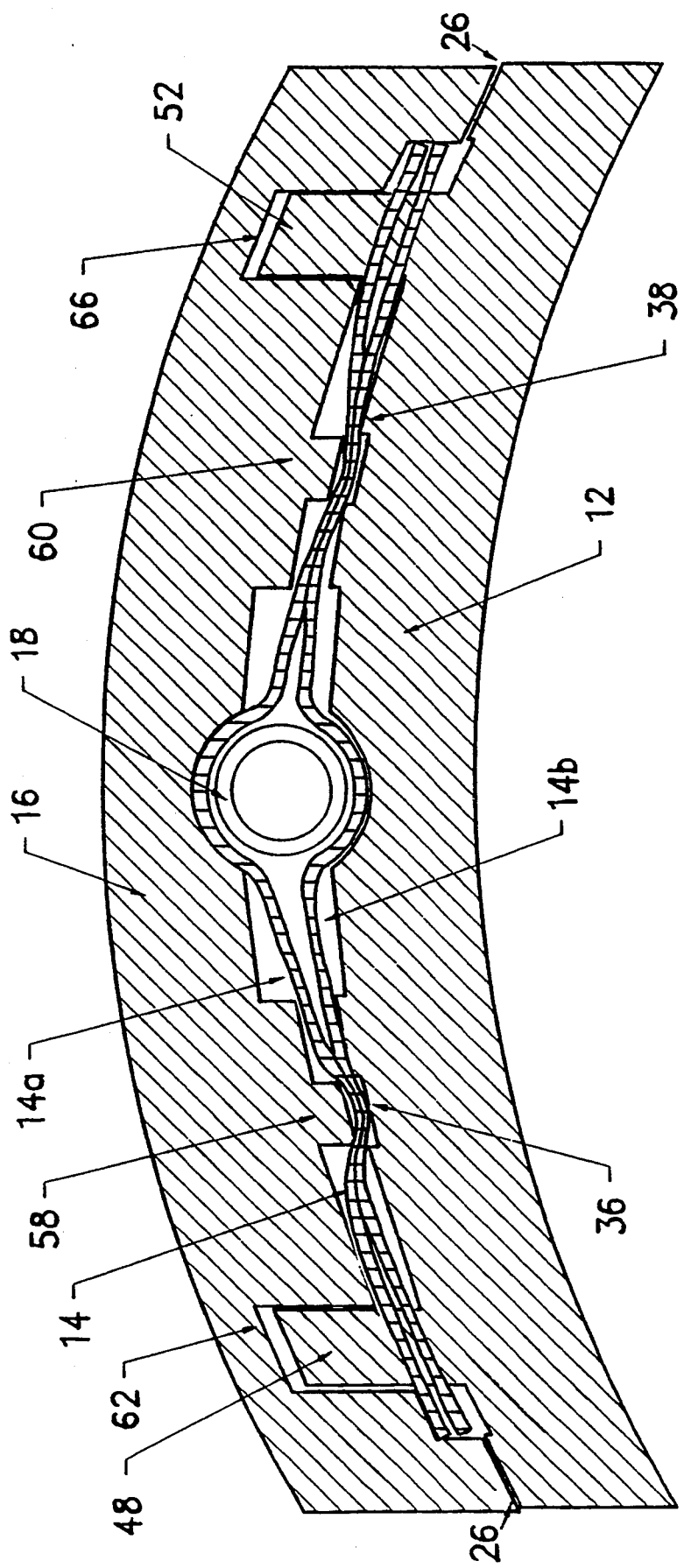
FIG. 3B is a cross-sectional view showing the two plates connected together and holding the folded membrane therebetween.
Figure 4:
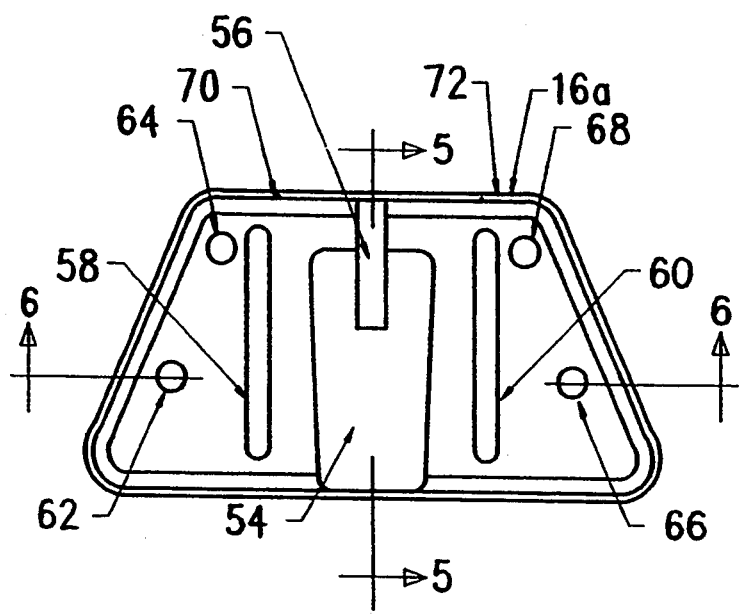
FIG. 4 is a plan view looking at the internal surface of the plate used in the medical valve of this invention.
Figure 5:
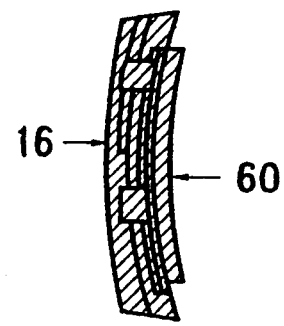
FIG. 5 is a cross-sectional view taken along 5—5 of FIG. 4.
Figure 6:
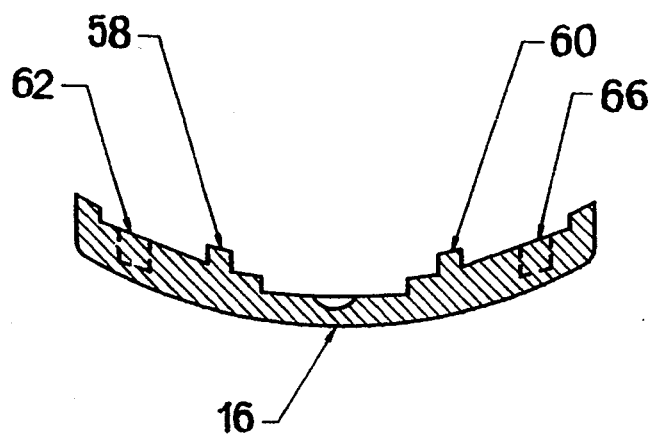
FIG. 6 is a cross-sectional view along 6—6 of FIG. 4.
Figure 7:
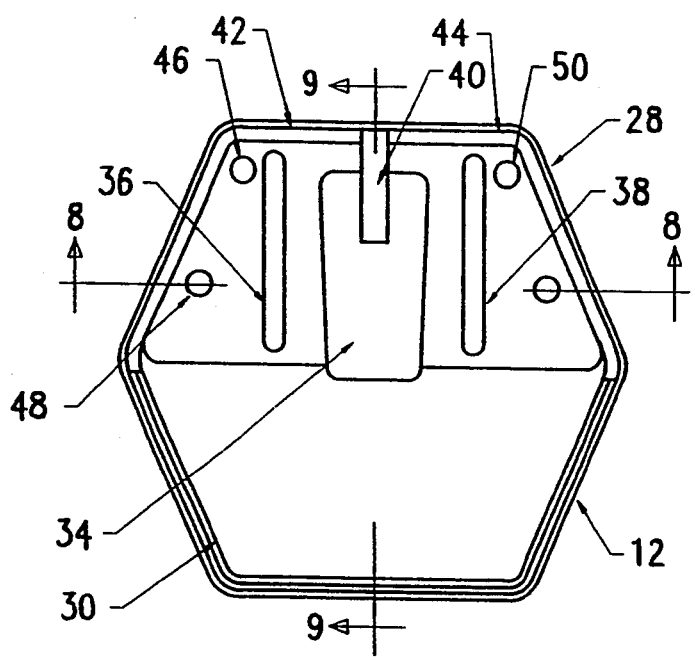
FIG. 7 is a plan view showing the internal surface of the base plate used in the medical valve of this invention.
Figure 9:
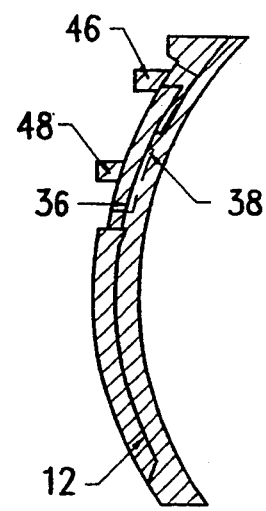
FIG. 9 is a cross-sectional view taken along 9—9 of FIG. 7.
Figure 8:
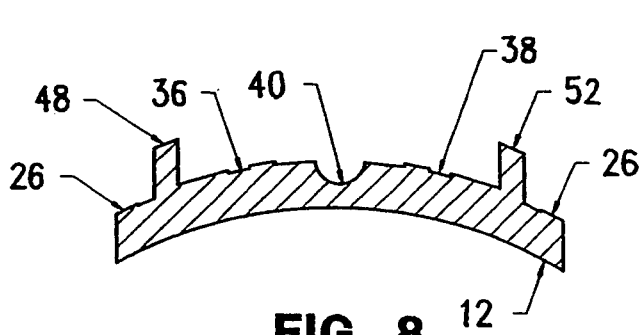
FIG. 8 is a cross-sectional view taken along line 8—8 of FIG. 7.
Figure 15:
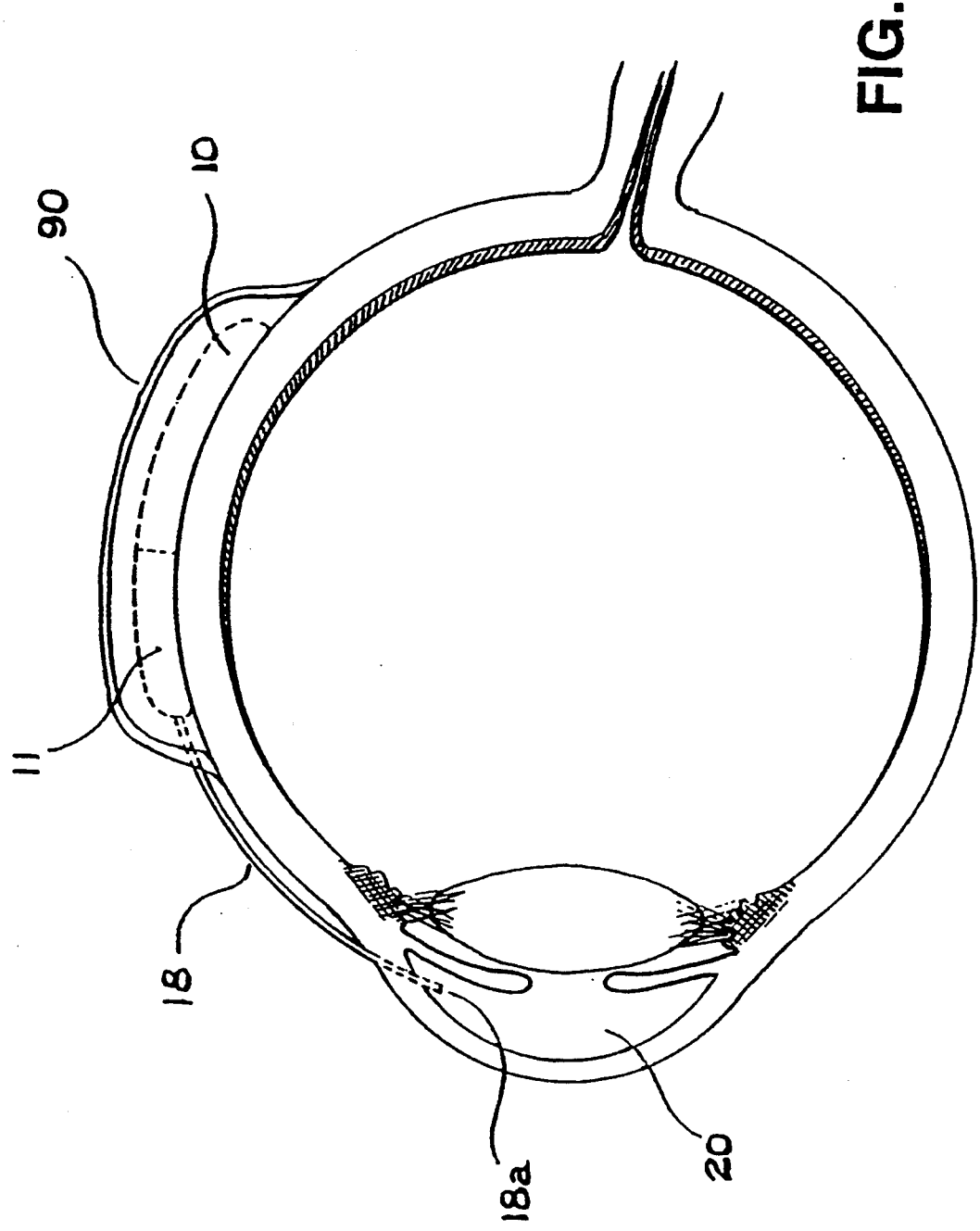
FIG. 15 is a cross-sectional view of the eyeball of the patient with the medical valve of this invention implanted therein.

As best illustrated in FIG. 1, the medical valve 10 of this invention includes a base plate 12, a flexible, siliconized rubber membrane 14, a top plate 16, and a siliconized rubber inlet tube 18. The membrane 14 is folded to form a pair of essentially identically shaped membrane members 14a and 14b. The membrane members 14a and 14b are placed between aligned and spaced apart top plate 16 and base plate 12 as illustrated in FIG. 3A and these plates are pressed together and interlocked as illustrated in FIG. 3B to hold the membrane members in position. The inlet tube 18 extends from the plates 12 and 16 so that its free end 18a may be surgically inserted into the intraoccular chamber 20 of the eye as illustrated in FIG. 15.

Figure 2:
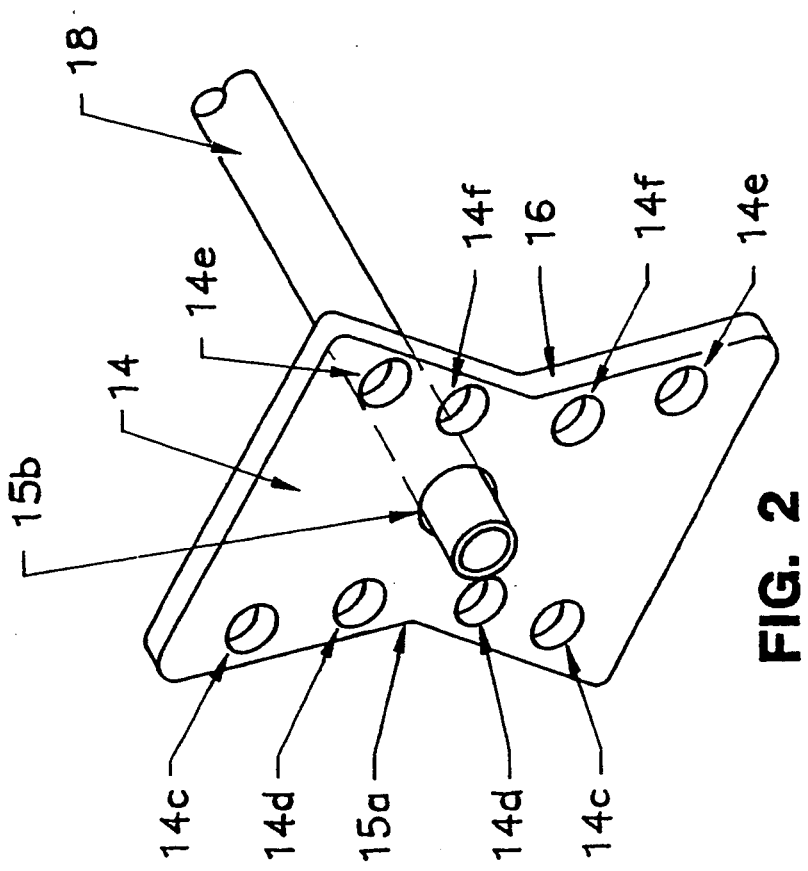
FIG. 2 is a perspective view of an unfolded membrane, with a tube extending outwardly from its backside.
Figure 2A:
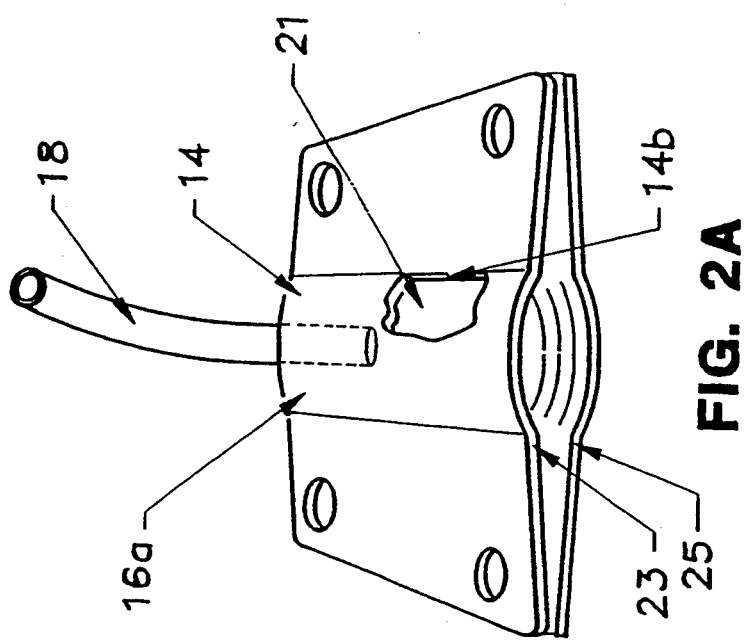
FIG. 2A is a perspective view of the membrane folded to form a trapezoidal chamber, showing the slit-like opening with its lips parted to allow fluid to flow from the chamber.

The membrane 14 is originally in a non-folded condition as shown in FIG. 2, and it has a hourglass-like shape narrowing at the central section 15a and then expanding outwardly therefrom in both directions. The membrane 14 has a thickness ranging between 0.004 and 0.007 inch, preferably between 0.005 and 0.006 inch. There is a central opening 15b in the member 14 in which the inlet tube 18 is inserted and four spaced apart openings 14c, 14c', 14d, 14d', 14e, 14e', 14f, and 14f' along its opposed irregular sides These holes 14c through 14f and 14c' through 14f' have a diameter of approximately 0.02 inch. A suitable siliconized rubber material for use as the membrane 14 and inlet tube 18 is made by Dow Corning Corporation, Medical Products, identified by the tradename Silastic, product No. 602–105.

The base plate 12 has a generally hexagonal configuration with a raised ridge 26 extending above the perimeter of the plate. The plate 12 is divided into a forward section 28 and a rear section 30. The portion of the ridge 26 surrounding the rear section 30 forms a distribution area 32 which receives aqueous humor from the eye. This distribution area 32 preferably ranges between about 0.119 and about 0.200 square inch.

The forward section 28 is raised above the distribution area 32 and it includes a centrally located depression 34 of a generally trapezoidal configuration. On each side of this depression, running along substantially its entire length, are two grooves 36 and 38. At the one end 34a of the depression 34 is a semi-cylindrical indentation 40 which receives the tube 18 and on each side of this indentation are two tiny orifices 42 and 44 having a diameter of about 0.02 inch. On the outside of each of the two grooves 36 and 38 are a pair of raised pins 46 and 48 and 50 and 52, respectively.

The top plate 16 is a four-sided member having a centrally located trapezoidal depression 54 therein with a semi-cylindrical indentation 56 along its one side 16a. There are a pair of elongated finger elements 58 and 60 extending downwardly which interlock, respectively, in the grooves 36 and 38 in the base plate 12 when the two plates are pressed together. There are pairs bores 62 and 64 and 66 and 68, respectively, of on the outside each of the fingers 58 and 60 which receive the pairs of pins 46 and 48 and 50 and 52 in the base plate 12 when the top plate 16 and base plate are aligned and pressed together. There are two small orifices 70 and 72 in the top plate 16 which are in registration with the orifices 42 and 44 when the base plate and top plate are joined together.

Both the top and base plates 12 and 16 have a segmented spherical shape so that they conform to the curvature of the eye ball. Both the plates 12 and 16 and the tube 18 are made of a material that will not be rejected by the body. Suitable materials from which to make the plates 12 and 16 are siliconized rubber, polyproylene, and polymythlmethyl acrelate (PMMA).

Figure 10:
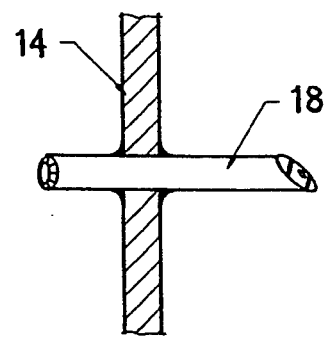
FIG. 10 is an enlarged cross-sectional view showing the way the tube is connected to the membrane
Figure 11:
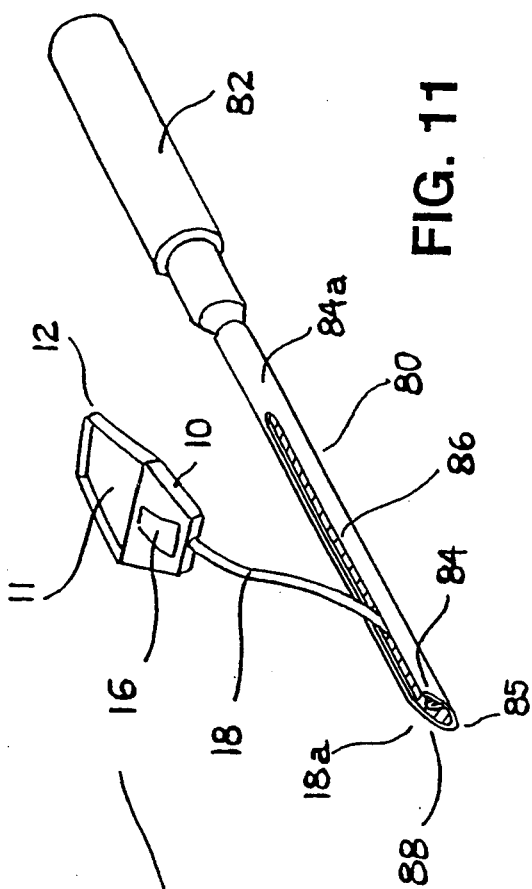
FIG. 11 is a perspective view a novel surgical instrument of this invention used to insert the tube from the valve into the intraoccular chamber of the eye.
Figure 12:
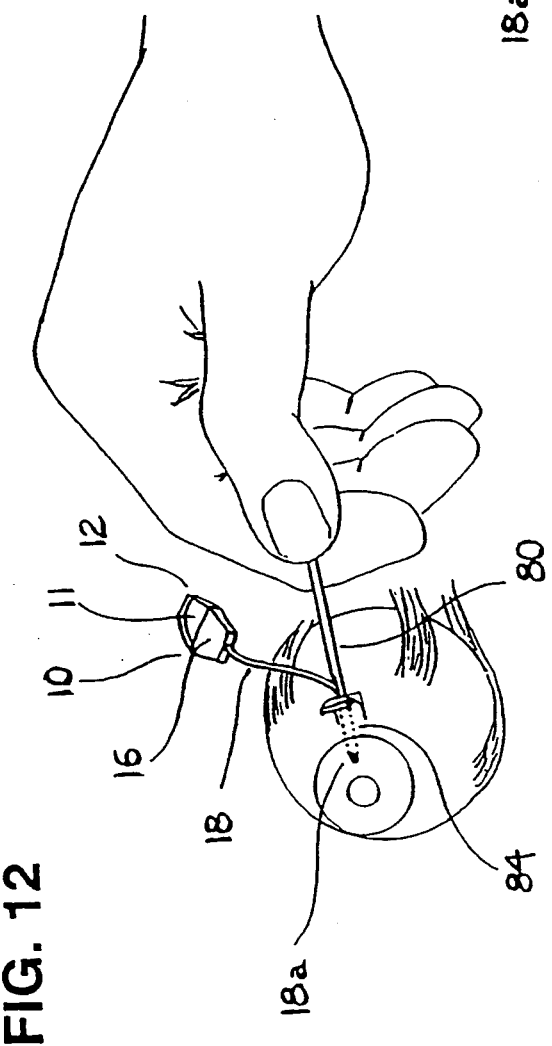
FIG. 12 is a schematic view showing the valve of this invention being surgically implanted in the eye of a patient using the instrument shown in FIG. 11.

FIG. 10 shows the way that the inlet tube 18 is bonded to the membrane 14. With the membrane 14 folded inwardly upon itself, it is placed between the top plate 16 and base plate 12 and these plates are interconnected together. This inlet tube 18 is inserted into the central opening 15b, with its outwardly extending section being placed between the indentations 40 and 56, respectively, in the plates 12 and 16. As shown in FIG. 10, an adhesive 17 is used to bond the tube 18 and the membrane 14. An example of a suitable adhesive is medical grade Silastic A made by Dow Corning Corporation.

One of the unique features of this invention is that, when the plates 12 and 16 are joined together, the membrane members 14a and 14b form between them in the space between the trapezoidal indentations 34 and 54 a chamber 21. At the inward edges 74 (FIG. 1) of these members 14a and 14b there is formed adjoining lips 23 and 25 that provide an elongated, slit-like opening 19 in the chamber 21 that is unlikely to be clogged by particulates. This slit-like opening 19 is normally closed because of the tension in the membrane members 14a and 14b, but opens when the pressure across the opening exceeds a predetermined value. When used as a glaucoma valve the differential in pressure must exceed 10 millimeters of mercury before the lips 23 and 25 part to open the valve. These lips 23 and 25 close immediately when the pressure differential is less than 10 millimeters of mercury.

The chamber 21 formed between the members 14a and 14b has a trapezoidal configuration. This is important because it makes the valve 10 very sensitive to slight changes in pressure. Due to the trapezoidal configuration of the chamber 21, the area of the inlet end of the chamber is larger than the area of the outlet end of the chamber. This creates a Bernoulli effect. Specifically, the incoming fluid fills the chamber 21 and the pressure increases to the point where the lips 23 and 25 of the membrane members 14a and 14b forming the slit-like opening 19 spread apart. The fluid then flows through the parted lips 23 and 25 of the membrane members 14a and 14b at a velocity which is substantially higher than the velocity of the fluid entering the chamber at the inlet end. Thus, the pressure is reduced almost instantaneously to close the valve 10. The incoming fluid causes the pressure in the chamber 21 to once again increase and the valve 10 again opens, with the pressure in the chamber deviating only slightly from a nominal value corresponding, or example, to the desired pressure to be maintained in the intraoccular chamber of the eye, namely 10 mm of Hg.

The medical valve 10 of this invention is easy to assemble. The membrane 14 is simply folded over and placed between the bas plate 12 and top plate 16 with these plates aligned and in registration so that, when they are pushed together, the interlocking members, including the pins 46, 48, 50 and 52 and bores 62, 64, 66, and 68, and grooves 36 and 38, and fingers 58 and 60, clamp the membrane members 14a and 14b firmly between the plates to form the valve body 11. The pins 46, 48, 50, and 52 pass through the holes 14c through 14f upon joining the plates 12 and 16 together. Ultrasonic welding bonds the plates 12 and 16 together.

As best illustrated in FIGS. 11 through 15, the medical valve 10 of this invention may be inserted into the eye of a patient by the use of a unique surgical instrument 80 consisting of a handle 82 and needle-like body member 84 having an elongated slot 86 in a side wall 81a of the needle-like member. The needle-like body member 84 terminates at the shape tip 85 which is beveled. The slot 86 allows the inlet tube 18 to be placed within the needle-like body member 84 lengthwise along a U-shaped channel 88 running along the longitudinal axis of the needle-like body member. The slot 86 and channel 88 each have a width that is essentially equal to the diameter of the inlet tube 18 so that, with the inlet tube lying in the channel, there is a snug, friction fit. Thus, fluid enters the open end of the tube and flows through the tube 18 rather than between the wall of the channel 88 and the wall of the tube. For use with the glaucoma valve 10 of this invention, the slot 86 has a width from 0.025 to 0.028 inch and a length of from 1.1 to 1.25 inch. The dimensions of t he slot and channel may, however, be varied depending on the application.

Figure 14:
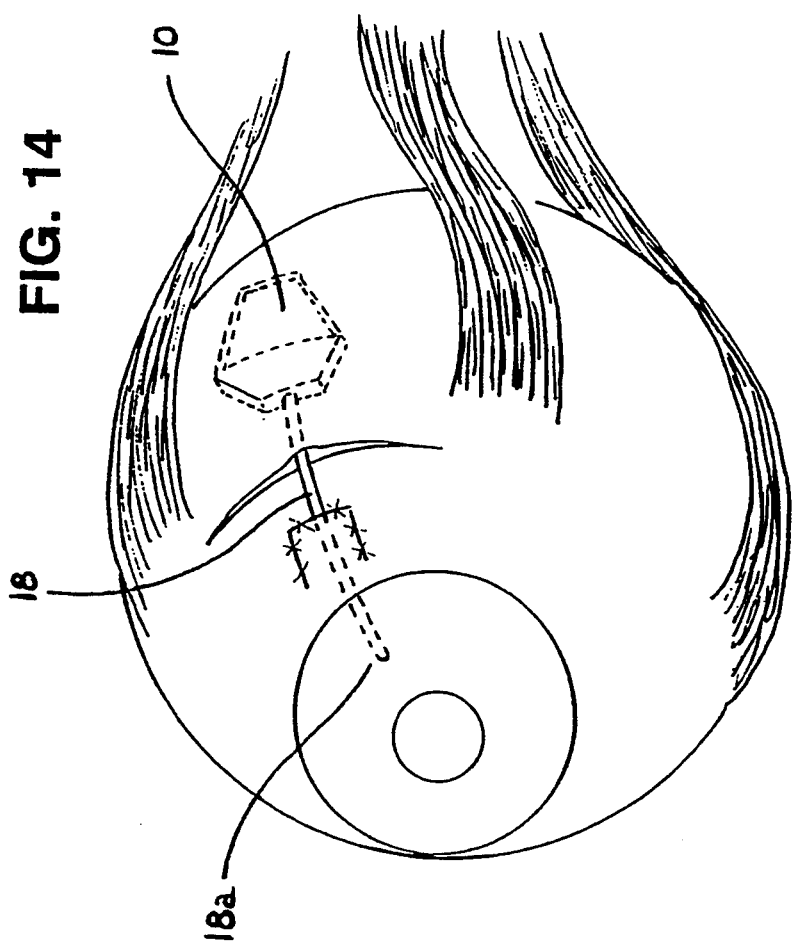
FIG. 14 is a perspective view of the valve implanted in the eye of a patient.
Figure 13:
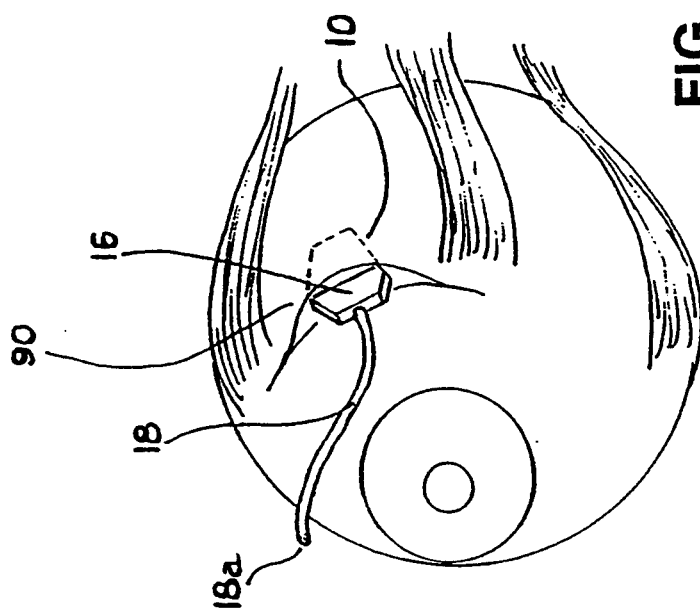
FIG. 13 is an enlarged perspective view of the medical valve of this invention partially implanted into the eye of the patient.

To us the instrument of this invention, with the tube 18 in the channel 88, the surgeon simply inserts the shape tip 85 of the instrument 80 into the eyeball to bring the inlet tube 18 into the intraoccular chamber 20 of the eye. The surgeon then simply withdraws the instrument. As he does this, the inlet tube 18 remains in the eye, with the surrounding tissue grasping the inlet tube as the instrument 80 is withdrawn. The valve body 11 is then placed beneath a sclara flap 90 (FIGS. 13 and 14) which is cut from the exterior of the eye ball. The flap 90 is then placed over the valve body 11 and then sutured in position as shown in FIG. 14. The aligned orifices 42 and 44 and 70 and 72, respectively in plates 12 and 16, allow the surgeon to suture the valve body 11 to the eye ball. This allows any overflow of aqueous humor flowing from distribution area 32 to seep beneath the valve body 11.

Figure 16:
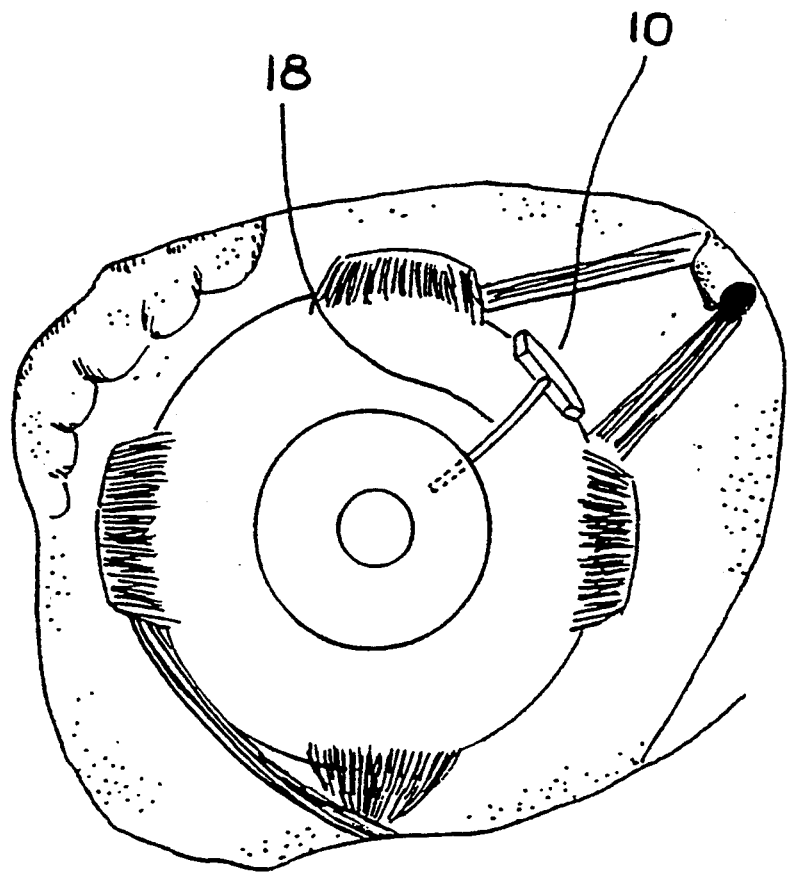
FIG. 16 is a front elevational view of an eye ball with the medical valve of this invention positioned at the desired location on the exterior of the eyeball.

Within a short period of time after the operation, a bleb is formed around the valve body 11. A bleb is a tissue membrane that traps the aqueous humor collecting in the distribution area 32 or under the valve body 11. This entrapped fluid is then slowly absorbed into the body of the patient. With the valve 10 implanted in the patient, as illustrated in FIGS. 15 and 16, pressure within the intraoccular chamber 20 forces the aqueous humor through the inlet tube 18 into the trapezoidal chamber. When the chamber is filled and the pressure in the intraoccular chamber 20 exceeds 10 millimeters of mercury, the lips 23 and 25 formed by the overlying members 14a and 14b spread apart, but only for such time period as this differential pressure exists. Once the differential pressure is below 10 millimeters of mercury, the membrane members 14a and, being under tension, close off the slit-like opening 19 automatically so that aqueous humor no longer will escape from the intraoccular chamber 20, thereby avoiding hypotony.

SCOPE OF THE INVENTION

The above description discloses the best mode contemplated of carrying out the present invention. This invention is, however, susceptible to modifications and alternate constructions from the embodiment shown in the drawing and described above. Consequently, it is not the intention to limit this invention to the particular embodiments disclosed. On the contrary, the intention is to cover all modifications and alternate constructions coming within the spit it and scope of the invention as generally expressed by the following claims:

I claim:

1. A medical valve including
means holding in tension a pair of overlying elastic membranes which form therebetween a chamber having an elongated, slit-like opening along adjoining, overlapping edges of the membranes, said opening expanding and contracting in response to changes in pressure in the chamber, and
an inlet tube in communication with the chamber at a point remote from the opening.

2. The medical valve of claim 1 including a plate which has an enlarged surface that serves to collect fluid escaping from the opening.

3. The medical valve of claim 1 wherein the chamber has a predetermined configuration so that its cross sectional area near the point where the inlet tube is in communication with the chamber is larger than the cross sectional area of the chamber near the opening.

4. The medical valve of claim 3 wherein the chamber has a trapezoidal configuration.

5. A medical valve including
a pair of plates holding in tension a pair of overlying membranes which form therebetween a chamber having an elongated, slit-like opening along adjoining edges of the membranes,
said opening normally being closed by the tension of the membranes but responding to a differential in pressure across the opening in excess of 10 millimeters of mercury to open and remain open as long as said differential in pressure exists, and
an inlet tube in communication with the chamber at a point remote from the opening.

6. A medical valve including
a pair of plates holding in tension a membrane which is folded into a pair of overlying members which form therebetween a chamber,
said edges being aligned and adjoining to form lips of an elongated slit-like opening having a length ranging between 2,74 and 3.81 millimeters,
said plates each having complimentary depressions therein of identical trapezoidal configurations and interlocking means connecting the plates together,
said plates with the folded member therebetween upon being joined together interlocking and holding the membrane in position under tension which is essentially equal across the width of the membrane, said membrane conforming in shape to the trapezoidal depression upon fluid filling the chamber,
said chamber having opposed parallel sides and opposed non-parallel sides, with one of said parallel sides being near an edge of one of the plates and the other parallel side being inwardly from said edge of one of said plates, said opening lying along the parallel side which is inwardly,
an inlet tube in communication with the chamber connected to the parallel side which is near the edge of the one plate, and
one of said plates having a section with an enlarge surface area that serves to collect and distribute over said surface area the fluid escaping from the opening.

7. The medical valve of claim 6 wherein said enlarged surface has a surface area ranging between 0.119 and 0.200 square inch.

8. A medical valve including
membrane means under tension forming a chamber having an elongated slit-like opening therein which is normally closed by the tension in the membrane means, and
inlet tube means in communication with the chamber that allows fluid to flow into the chamber, with the membrane means expanding to open the slit-like opening when the fluid pressure in the chamber exceeds a predetermined value.

9. The medical valve of claim 8 wherein the chamber has a trapezoidal configuration providing a narrow side and a wide side, with the tube connected to the wide side and the opening along the narrow side.

* * * * *